(12) United States Patent
Schmidt et al.

(10) Patent No.: US 8,235,901 B2
(45) Date of Patent: Aug. 7, 2012

(54) FOCUSED ULTRASOUND SYSTEM WITH FAR FIELD TAIL SUPPRESSION

(75) Inventors: Rita Schmidt, Givataim (IL); Shuki Vitek, Haifa (IL)

(73) Assignee: Insightec, Ltd., Tirat Carmel (IL)

( * ) Notice: Subject to any disclaimer, the term of this patent is extended or adjusted under 35 U.S.C. 154(b) by 740 days.

(21) Appl. No.: 11/536,619

(22) Filed: Sep. 28, 2006

(65) Prior Publication Data
US 2008/0082026 A1    Apr. 3, 2008

Related U.S. Application Data

(63) Continuation of application No. 11/380,332, filed on Apr. 26, 2006, now abandoned.

(51) Int. Cl.
A61B 8/00    (2006.01)
(52) U.S. Cl. ............................ 600/439; 601/2
(58) Field of Classification Search .................. 600/439, 600/436; 601/2
See application file for complete search history.

(56) References Cited

U.S. PATENT DOCUMENTS

| | | | |
|---|---|---|---|
| 2,795,709 A | 6/1957 | Camp | |
| 3,142,035 A | 7/1964 | Harris | |
| 3,942,150 A | 3/1976 | Booth et al. | |
| 3,974,475 A | 8/1976 | Burckhardt et al. | |
| 3,992,693 A | 11/1976 | Martin et al. | |
| 4,000,493 A | 12/1976 | Spaulding et al. | |
| 4,339,952 A | 7/1982 | Foster | |
| 4,454,597 A | 6/1984 | Sullivan | |
| 4,478,083 A | 10/1984 | Hassler et al. | |
| 4,505,156 A | 3/1985 | Questo | |
| 4,526,168 A | 7/1985 | Hassler et al. | |
| 4,537,074 A | 8/1985 | Dietz | |
| 4,549,533 A | 10/1985 | Cain et al. | |
| 4,858,597 A | 8/1989 | Kurtze et al. | |
| 4,865,042 A | 9/1989 | Umemura et al. | |
| 4,888,746 A | 12/1989 | Wurster et al. | |
| 4,889,122 A | 12/1989 | Watmough et al. | |

(Continued)

FOREIGN PATENT DOCUMENTS
DE    4345308 C2    2/2001
(Continued)

OTHER PUBLICATIONS

PCT Partial International Search Report for PCT/IB2007/001079, Applicant Insightec Ltd, EPO Form P0455A, dated Sep. 25, 2007 (13 pages).

(Continued)

*Primary Examiner* — Long V. Le
*Assistant Examiner* — Ellsworth Weatherby
(74) *Attorney, Agent, or Firm* — Bingham McCuthen LLP

(57) ABSTRACT

A method for treating body tissue using acoustic energy includes identifying a target focal zone of tissue to be treated, delivering a first pulse of acoustic energy from a transducer to generate bubbles in a tissue region located distally, relative to the transducer, of a focal center of the target focal zone, and delivering a second pulse of acoustic energy from the transducer in the presence of the bubbles generated by the first pulse, the second pulse focused at the focal center to generate thermal ablation energy. In a further embodiment, a method of treating body tissue using ultrasound energy includes identifying a target focal zone to be treated and delivering a plurality of pulses of acoustic ablation energy to locations distributed symmetrically in or proximate a focal plane about the focal center of the target focal zone.

22 Claims, 5 Drawing Sheets

U.S. PATENT DOCUMENTS

| | | |
|---|---|---|
| 4,893,284 A | 1/1990 | Magrane |
| 4,937,767 A | 6/1990 | Reuschel et al. |
| 5,209,221 A | 5/1993 | Riedlinger |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,769,790 A | 6/1998 | Watkins et al. |
| 5,810,008 A | 9/1998 | Dekel et al. |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich et al. |
| 6,543,272 B1 | 4/2003 | Vitek |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,666,833 B1 | 12/2003 | Friedman et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 * | 8/2004 | Zhong et al. ............... 601/4 |
| 6,788,619 B2 | 9/2004 | Calvert |
| 6,790,180 B2 | 9/2004 | Vitek |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 * | 7/2006 | Kadziauskas et al. ........ 604/22 |
| 7,094,205 B2 | 8/2006 | Marmarelis |
| 7,128,711 B2 | 10/2006 | Medan et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 * | 9/2007 | Cathignol ................... 601/4 |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,686,763 B2 * | 3/2010 | Vaezy et al. .............. 600/439 |
| 7,699,780 B2 | 4/2010 | Vitek et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2003/0004439 A1 | 1/2003 | Pant et al. |
| 2003/0060820 A1 | 3/2003 | Maguire et al. |
| 2003/0187371 A1 * | 10/2003 | Vortman et al. ............. 601/3 |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0210134 A1 | 10/2004 | Hynynen et al. |
| 2005/0033201 A1 | 2/2005 | Takahashi et al. |
| 2005/0096542 A1 | 5/2005 | Weng et al. |
| 2005/0203444 A1 | 9/2005 | Schonenberger et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0058678 A1 | 3/2006 | Vitek et al. |
| 2006/0106300 A1 | 5/2006 | Seppenwoolde et al. |
| 2006/0173385 A1 | 8/2006 | Lidgren et al. |
| 2006/0206105 A1 | 9/2006 | Chopra et al. |
| 2006/0229594 A1 | 10/2006 | Francischelli et al. |
| 2007/0016039 A1 | 1/2007 | Vortman et al. |
| 2007/0055140 A1 | 3/2007 | Kuroda |
| 2007/0055181 A1 * | 3/2007 | Deem et al. ................. 601/2 |

| | | | |
|---|---|---|---|
| 2007/0098232 A1* | 5/2007 | Matula et al. | 382/120 |
| 2007/0167781 A1 | 7/2007 | Vortman et al. | |
| 2007/0197918 A1 | 8/2007 | Vitek et al. | |
| 2008/0027342 A1 | 1/2008 | Rouw et al. | |
| 2008/0031090 A1 | 2/2008 | Prus et al. | |
| 2008/0033278 A1 | 2/2008 | Assif | |
| 2008/0082026 A1 | 4/2008 | Schmidt et al. | |
| 2008/0108900 A1 | 5/2008 | Lee et al. | |
| 2008/0200845 A1* | 8/2008 | Sokka et al. | 604/22 |
| 2009/0088623 A1 | 4/2009 | Vortman et al. | |
| 2010/0056962 A1 | 3/2010 | Vortman et al. | |

FOREIGN PATENT DOCUMENTS

| | | |
|---|---|---|
| EP | 0031614 A1 | 7/1981 |
| EP | 0558029 A2 | 9/1993 |
| EP | 0875203 A2 | 11/1998 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | WO-0166189 A1 | 9/2001 |
| WO | WO-0180709 A2 | 11/2001 |
| WO | WO-02058791 A1 | 8/2002 |
| WO | 03/097162 | 11/2003 |
| WO | WO 03097162 A2 * | 11/2003 |
| WO | WO-03097162 A2 | 11/2003 |
| WO | WO-03098232 A2 | 11/2003 |
| WO | WO-2006025001 A1 | 3/2006 |
| WO | WO-2006087649 A1 | 8/2006 |
| WO | WO-2007073551 A1 | 6/2007 |
| WO | WO-2008050278 A1 | 5/2008 |
| WO | WO-2008119054 A1 | 10/2008 |
| WO | WO-2009055587 A1 | 4/2009 |

OTHER PUBLICATIONS

International Search Report & Written Opinion for International Application No. PCT/IB2007/001079, mailed Dec. 10, 2007 (16 pages).
Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).
Chen et al., "MR Acoustic Radiation Force Imaging: Comparison of Encoding Gradients."
Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. On Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. On Therapeutic Ultrasound, edited by E.S. Ebbini, U. of Minn. (Sep. 2009).
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.

* cited by examiner

FIG. 9
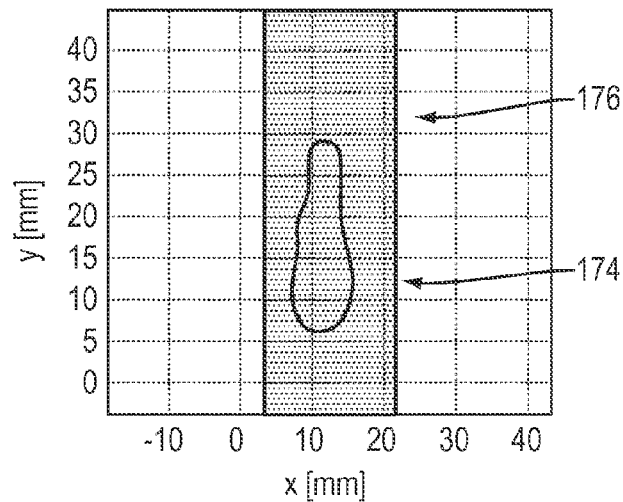
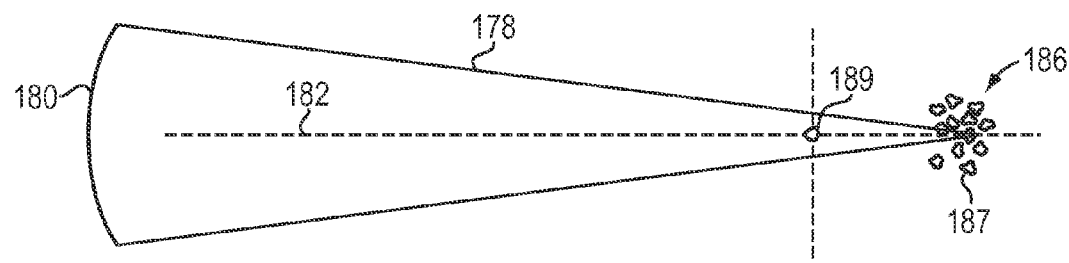
FIG. 10A
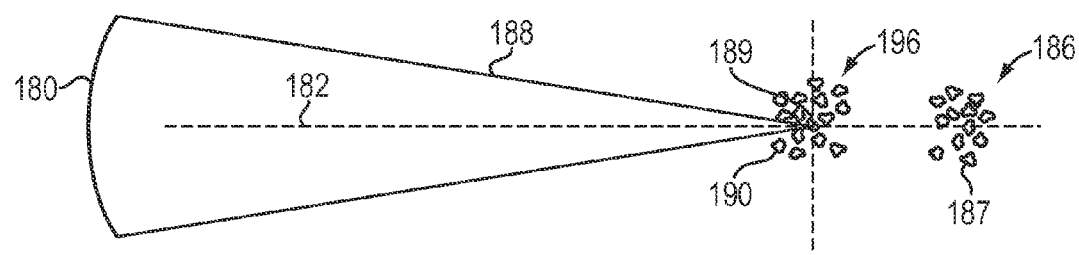
FIG. 10B
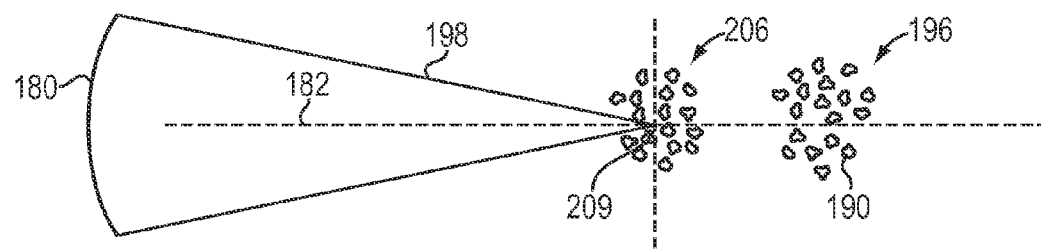
FIG. 10C

FOCUSED ULTRASOUND SYSTEM WITH FAR FIELD TAIL SUPPRESSION

RELATED APPLICATION DATA

This application claims the benefit of U.S. Utility patent application Ser. No. 11/380,332, filed Apr. 26, 2006, pursuant to 35 U.S.C. Section 120, and any other applicable laws. The aforementioned application is hereby incorporated by reference herein in its entirety.

FIELD OF INVENTION

The present invention relates generally to thermal treatment systems, and more particularly to systems and methods for delivering and controlling thermal energy dosing using an image-guided, focused ultrasound system.

BACKGROUND

It is well-known to use high intensity, focused acoustic wave energy, such as ultrasonic waves (i.e., acoustic waves having a frequency greater than about 20 kilohertz) to generate thermal ablation energy for treating internal body tissue, such as tumors. It is also well-known to employ a tissue imaging system (e.g., MRI) in order to guide the delivery of such high intensity ultrasound energy, and to provide real-time feedback. One such image-guided focused ultrasound system is the Exablate® 2000 system manufactured and distributed by InSightec Ltd, located in Haifa, Israel. (www.insightec.com).

By way of illustration, FIG. 1 is a schematic representation of a simplified image-guided, focused ultrasound system 100 used to deliver thermal energy to a target tissue mass 104 in a patient 110. The system 100 employs an ultrasound transducer 102 to deliver an acoustic energy beam 112 generated by a large number of individual piezoelectric transducer elements 116 mounted on a distal (outward) facing surface 118 (shown in FIG. 2) of the transducer 102. The transducer 102 is geometrically shaped and positioned in order to focus the ultrasonic energy beam 112 at a three-dimensional focal zone located within the target tissue mass 104. While the illustrated transducer 102 has a spherical cap configuration, there are a variety of other geometric transducer designs that may be employed.

In particular, ultrasound is vibrational energy propagated as a mechanical wave through a target medium (e.g., body tissue). In the illustrated system 100, the individual transducer elements 116 collectively generate the mechanical wave (or "acoustic beam") 112 by converting respective electronic drive signals received from a system controller 106 into mechanical motion. Wave energy transmitted from the individual elements collectively forms the acoustic energy beam 112 as it converges on the target tissue mass 104. Within the focal zone, the wave energy of the beam 112 is absorbed (attenuated) by the tissue, thereby generating heat and raising the temperature of the target tissue mass to a point where the tissue cells are killed ("ablated"). An imager (e.g., an MRI system) 114 is used to generate three-dimensional images of the target tissue region 104 both before, during and after the wave energy is delivered. For example, the images may be thermally sensitive, so that the actual thermal dosing boundaries (i.e., the geometric boundaries and thermal gradients) of the target tissue region may be monitored.

The transducer 102 may be focused at different locations within the target tissue region 104 by mechanical movement, including orientation of the transducer. Electronic "beam steering" may additionally or alternatively be used to change location of the focal zone by making corresponding changes in the attributes (e.g., phase, amplitude, frequency) and the individual transducer element drive signals. In a typical tumor ablation procedure, the transducer 102 delivers a series of discrete pulses of high intensity acoustic wave energy, each for a sufficient duration to generate tissue-destroying heat in a given focal zone. The energy pulses are sequentially focused at a number of differing focal zones located in close proximity to one another, until complete destruction ("ablation") of the target tissue region 104 is achieved. Further information regarding image-guided focused ultrasound systems and their use for performing non-invasive tissue (e.g., tumor) ablation procedures may be found, for example, in U.S. Pat. Nos. 6,618,620, 6,582,381, and 6,506,154, each of which is hereby incorporated by reference.

FIG. 3 is an MRI image of the heat intensity distribution 125 caused by a nominal "sonication" (delivery of acoustic energy) of a target tissue area using a spherical cap transducer (such as transducer 102 in system 100 of FIGS. 1 and 2). The heat intensity distribution 125 is shaped by the interaction of the acoustic beam with the tissue, as well as the frequency, duration, and power (i.e., mechanical pressure) of the beam. More particularly, the wave energy converges as it propagates (from left to right in FIG. 3) through a "near field" region 119 to a focal zone 120, which tends to have an elongate, cylindrical shape. The conversation of wave energy to heat is most intense in the focal zone 120, due to the convergence (and collisions) of the individual waves, and can be generally equated with the tissue destruction, or "ablation" volume. Notably, some of the wave energy is absorbed in the near field region 119, especially in the area adjacent to the focal zone 120. A further portion of the wave energy passes through the focal zone and is absorbed in a "far-field" region 122, which refers generally to the tissue region located distally of the focal zone relative to the transducer. Although the waves that pass through (or are reflected from) the focal zone 120 tend to diverge in the far field region 122, to the extent any such far field energy absorption occurs in a concentrated area, it can result in undesirable and potentially harmful (and painful) heating and necrosis of otherwise healthy tissue.

As described in PCT publication WO 2003/097162, which is hereby incorporated by reference, it is possible to increase the effectiveness of thermal dosing of a target tissue region by delivering one or more relatively high pressure, short duration acoustic energy pulses to generate air bubbles in tissue located in the intended focal zone just prior to delivering a regular "ablation energy" wave pulse. The presence of the bubbles serves to increase the mechanical-to-thermal energy conversion in the tissue, which, along with the added reflection and scattering of the main acoustic beam, has the positive effect of reducing the overall amount of potentially detrimental far-field energy absorption. However, as shown in FIGS. 4 and 5, while the overall amount of far-field energy is decreased by the presence of the bubbles at the focal zone center, a far greater concentration of the remaining far field energy is concentrated along a central beam propagation axis 124, extending distally from a center focal plane 126 of the "enhanced ablation" focal zone 128. This thermal energy concentration has the appearance of a thermal "tail" 130 that tapers into a highly undesirable stick portion 132 (best seen in FIG. 5), thereby elongating the effective tissue ablation region 134, and resulting in an even higher temperature in a close-in portion of the far field region 136 than occurs during a non-bubble enhanced sonication.

SUMMARY OF THE INVENTION

In accordance with one embodiment, a procedure for treating tissue using acoustic energy includes identifying a three-dimensional target tissue ablation zone, delivering a relatively short duration pulse of acoustic energy from a transducer to generate bubbles in tissue located in a distal portion (relative to the transducer) of the target ablation zone, and, in the presence of the bubbles, delivering a substantially longer duration pulse of acoustic energy to a more proximally located focal center of the target ablation zone. In particular, the bubbles generated by the initial, short duration pulse form a "bubble mask" that suppresses formation of a far-field thermal ablation tail that would otherwise occur if the bubbles had been generated at the focal center, as is done in a conventional enhanced-ablation procedure. Because, bubbles generated by the initial, "bubble formation" pulse will rapidly dissipate, and it may be desirable to deliver additional bubble formation pulses in-between relatively longer "ablation energy" pulses, in order to re-establish and/or maintain the bubble mask in the distal portion of the target tissue ablation zone.

By way of example, in a procedure carried out according to one embodiment, a short duration (e.g., 0.1 second) bubble formation pulse is delivered to a distal portion of the target ablation zone, e.g., approximately 10 mm distal of the focal center relative to the transducer. The bubble formation pulse is immediately followed by a relatively longer duration (e.g., 0.5 second) ablation energy pulse delivered to the focal center. Following a delay (e.g., of 2.0 seconds) to allow for bubbles generated in the focal center during the ablation energy pulse to dissipate, the cycle is repeated by delivering another a short duration (e.g., 0.1 second) bubble formation pulse to the distal portion of the target ablation zone, followed by another longer duration (e.g., 0.5 second) ablation energy pulse delivered to the focal center, and another (e.g., 2.0 second) off period. This series of "bubble-masked" sonications may be repeated until ablation of the entire the target tissue zone is achieved. In a variation of this embodiment, bubbles generated by the ablation energy pulse are used as a bubble mask for an ensuing ablation energy pulse focused proximally of the immediately preceding pulse.

In accordance with another embodiment, a procedure for treating tissue using acoustic energy includes identifying a three-dimensional target tissue ablation zone, and then delivering respective ablation energy pulses to focal locations distributed about a focal center of the target ablation zone. By way of non-limiting example, a series of three to five ablation energy pulses may be delivered, each for approximately 0.5 seconds followed by (e.g., a 2.0 second) delay, to respective focal locations distributed in a symmetrical pattern about the focal center of the target ablation zone. The sequence of distributed ablation energy pulses may be repeated, whether in a same or differing pattern, until ablation of the entire the target tissue zone is achieved.

In accordance with yet another embodiment in which features of the previously-described embodiments are combined, a procedure for treating tissue using acoustic energy includes identifying a three-dimensional target tissue ablation zone, and then delivering respective pairs of bubble formation and ablation energy pulses in a pattern distributed about a focal center of the target ablation zone.

Other and further features and aspects of the various embodiments will become apparent from the following detailed description of the illustrated embodiments.

BRIEF DESCRIPTION OF THE DRAWINGS

Embodiments of the invention are illustrated by way of example, and not by way of limitation, in the figures of the accompanying drawings, in which:

FIG. 9 illustrates a tissue ablation zone resulting from a sonication carried out according to the embodiment of FIGS. 6 and 7, resulting in thermal tail suppression.

FIGS. 10A-C are a cut-away schematic side views illustrating delivery of respective bubble-formation and ablation energy pulses to successive target focal zones located along a propagation axis of a transducer, in accordance with another embodiment of the invention.

DETAILED DESCRIPTION OF THE ILLUSTRATED EMBODIMENTS

Figure 1:
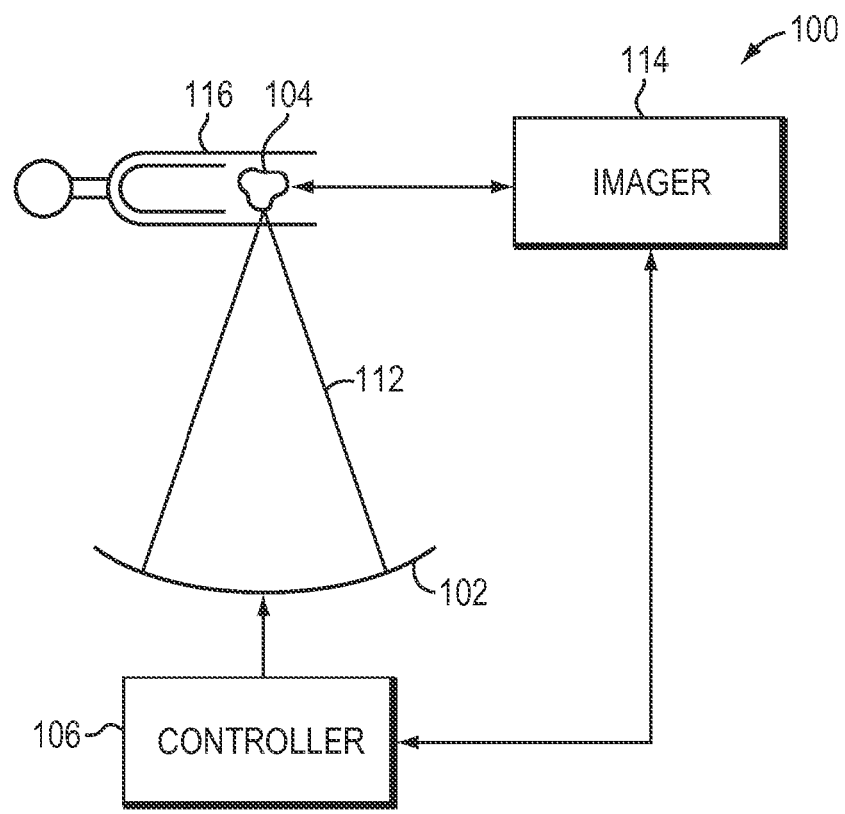
FIG. 1 is simplified schematic diagram of a focused ultrasound treatment system for providing thermal energy dosing of a target tissue region in a patient.
Figure 2:
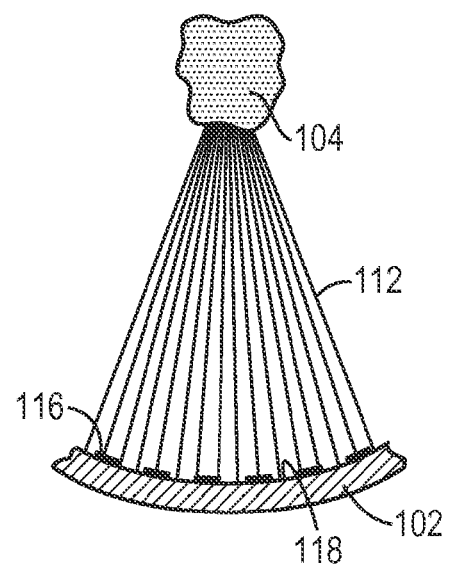
FIG. 2 is a cut-away schematic side view of the transducer in the system of FIG. 1, illustrating the concentrated emission of focused ultrasonic energy to a targeted tissue structure.
Figure 3:
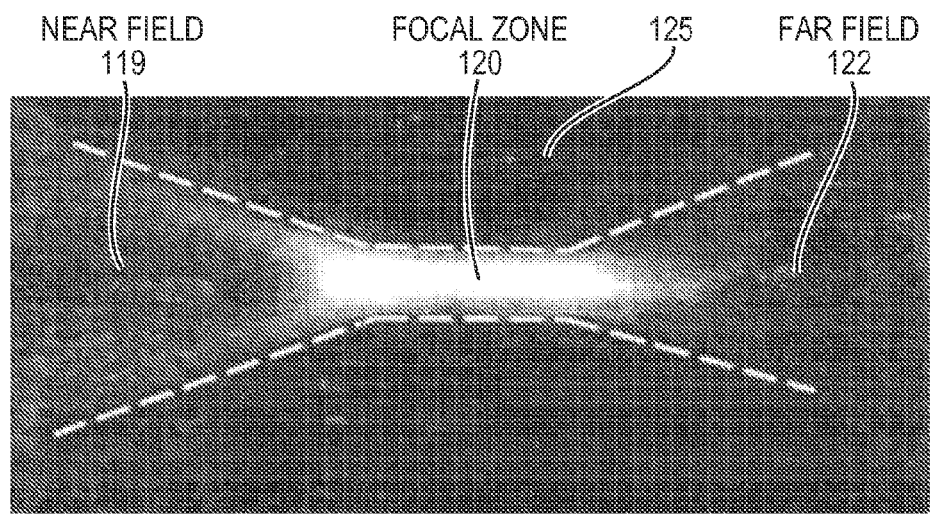
FIG. 3 is an image obtained by a magnetic resonance imaging (MRI) system of a heating phantom in a target tissue region during delivery of converging (low power) acoustic energy from a transducer (not shown), illustrating formation of a heat-intensity focal zone.
Figure 4:
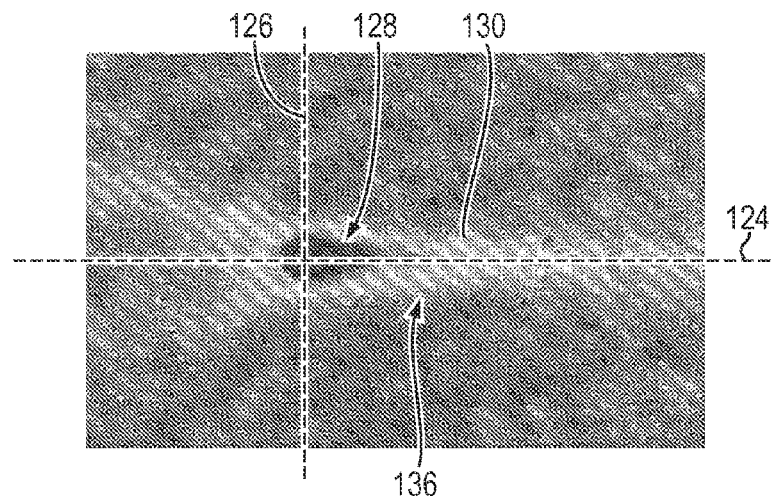
FIG. 4 is an MRI thermal profile image of a cross-section of an area of tissue being heated in a conventional, bubble-enhanced sonication, including illustrating a heat-intensity focal zone at its highest temperature point.
Figure 5:
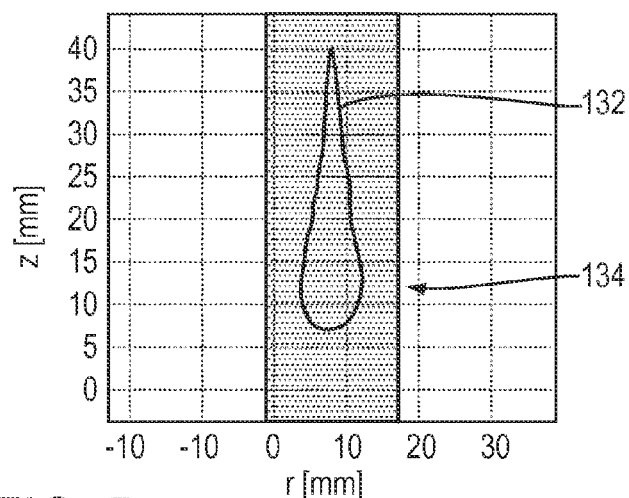
FIG. 5 illustrates a tissue ablation zone resulting from a conventional, bubble-enhanced sonication, such as that illustrated in FIG. 4.

It will be appreciated that embodiments of the invention may be software and/or hardware implemented in a control system of a focused ultrasound system, e.g., such as controller 106 of system 100 shown in FIG. 1. Further embodiments of the invention include methods for using a focused ultrasound system to deliver converging acoustic wave energy to a selected three-dimensional focal zone in a target tissue region for providing controlled thermal dosing of body tissue, which methods may manually controlled, or which may be fully or partially automated. In particular, embodiments of the invention may be implemented in systems and methods for providing and controlling a series of treatment sonications for ablating a target tissue region, and may involve one or both of user input and control (e.g., operational commands entered through a user interface), and automated functions performed by the system controller. In accordance with this general understanding, the following detailed description refers to a "controller" of a focused ultrasound system for purposes of illustration, and not limitation. It will be apparent to those skilled in the art that the described embodiments may be readily implemented in such a controller without requiring specific instructions for such implementation to be provided herein. Further, the particular control aspects and features of a system controller configured for performing and/or assisting in the performance of the illustrated and described embodiments will be apparent from the descriptions themselves.

Figure 6:
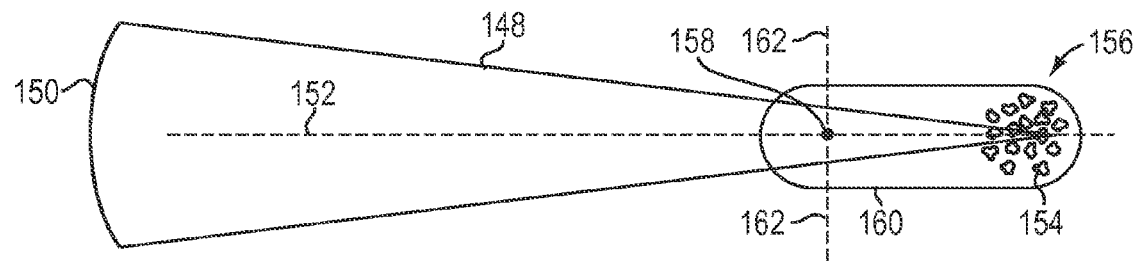
FIGS. 6 and 7 are a cut-away schematic side views illustrating delivery of respective bubble-formation and ablation energy pulses to a target focal zone, in accordance with one embodiment of the invention.

Referring to FIG. 6, in one embodiment, a method for treating tissue using acoustic energy includes delivering a first, relatively short duration, high power (i.e., wave pressure) pulse of acoustic wave energy 148 from a transducer 150 along a transducer propagation axis 152 to generate tissue bubbles 154 in a distal region 156, relative to the transducer 150, of a target tissue ablation focal zone 160. This initial bubble-formation pulse 148 does not necessarily make a significant contribution to the overall ablation, and preferably has a relatively short duration so as to not form its own far-field thermal tail. By way of non-limiting examples, the duration of the bubble-formation pulse 148 may be in a range from 0.05 to 0.15 seconds, and in one embodiment is approximately 0.1 seconds. In various embodiments, the bubble-formation pulse 148 is focused along the propagation axis 152 in a range of 5 mm to 15 mm distal of a focal plane 162 lying normal to the propagation axis 152 and including the focal center 158. In one such embodiment, propagation axis is also the focal axis of the focal zone 160, and the bubble-formation pulse 148 is focused along the propagation axis 152 approximately 10 mm distal of the focal plane 162 including the focal center 158.

Figure 7:
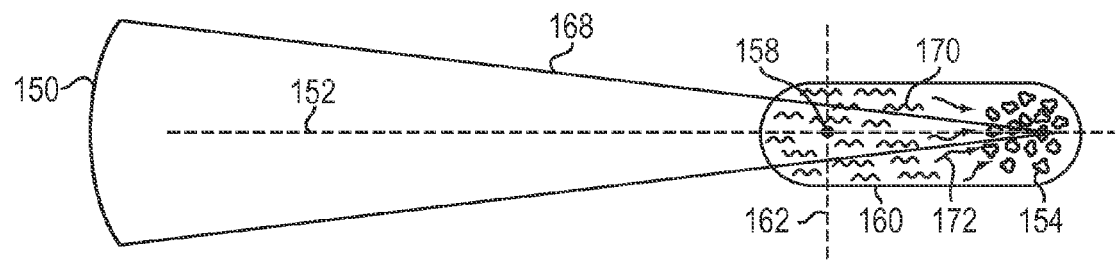

Referring to FIG. 7, immediately following delivery of the bubble-formation pulse 148, and in the presence of the bubbles 154, a further, substantially longer duration pulse of acoustic wave energy 168 is delivered from the transducer 150 along the transducer propagation axis 152 to apply thermal ablation energy 170 to the target focal zone 160. The ablation energy pulse 168 is focused at the focal center 158 and is in a range of between approximately 0.2 to 1.0 seconds in duration, e.g., approximately 0.5 seconds in one embodiment. Notably, the relative positioning/focusing of the transducer 150, and the delivery of respective bubble formation and ablation energy pulses 148 and 168 are under the control of a system controller (not shown). The respective target focal zone 160 may be identified by the controller based, at least in part, on images provided from an imaging system and operator input provided through a user interface (not shown). A respective time duration and power level of the bubble-formation and ablation energy pulses 148 and 168 may be selected by user input, or may be automatically determined by the controller based, at least in part, on characteristics of the tissue located in or near the focal zone 160. The focal center 156 of the bubble-formation pulse 148 may also be selected by user input or automatically determined by the controller, and may be a predetermined distance from the focal center 158 along the transducer propagation axis 152, e.g., 10 mm distal of the focal center 158 in one embodiment.

Figure 8:
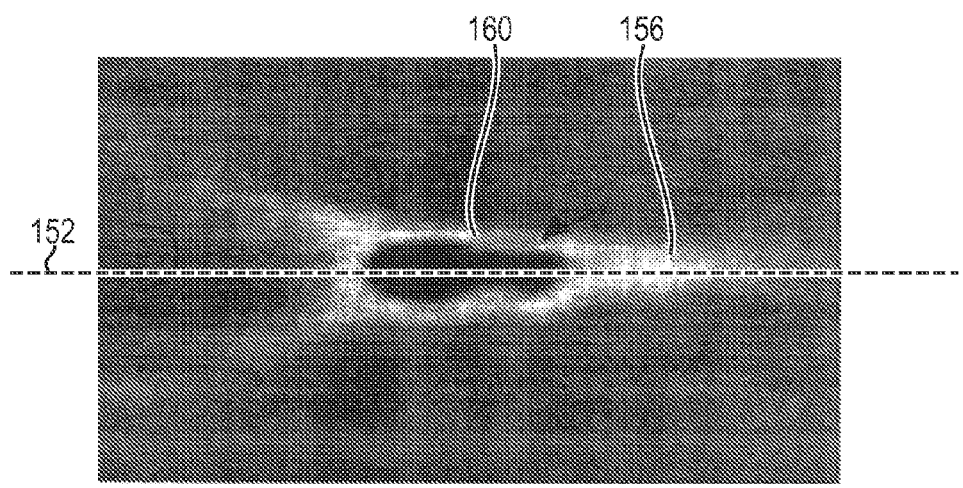
FIG. 8 is an MRI thermal profile image of tissue heated during a sonication carried out according to the embodiment of FIGS. 6 and 7, illustrating a heat-intensity focal zone at its highest temperature point.

As seen in FIGS. 8 and 9, it has been observed by the present inventors that focusing the bubble formation pulse 148 of the enhanced ablation procedure in a distal region 156 of the target focal zone 160 allows the bubbles 154 to act as a "bubble mask" (indicated by arrows 172 in FIG. 7) that suppresses formation of a far-field thermal tail in the resulting ablation 174. While a certain amount of the acoustic energy of the ablation pulse 168 will still pass through the focal zone 160 and into the far field region 176, the bubble mask 154 prevents this remaining energy portion from forming a potentially harmful thermal tail.

Figure 12:
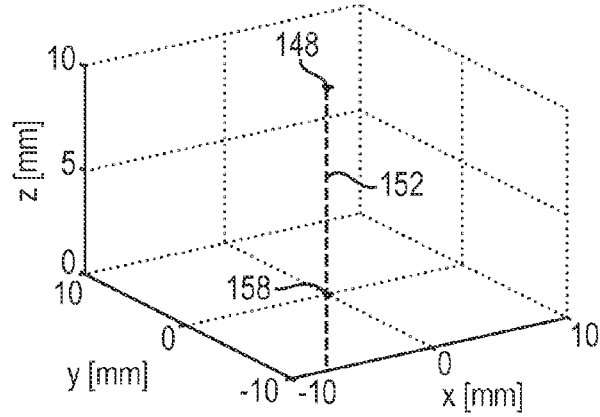
FIG. 12 is a schematic illustration of a three-dimensional coordinate system having an x-y plane at a focal plane of a target tissue ablation zone, with the z-axis extending in a distal direction from the focal plane, illustrating the focal centers of respective bubble-generating and tissue ablation pulses delivered in accordance with the embodiment of FIGS. 6 and 7.

Because the bubble mask 154 generated by the bubble formation pulse 148 will rapidly dissipate, and it may be desirable to deliver additional bubble formation pulses to the distal region in between relatively longer duration ablation energy pulses 168, in order to re-establish and/or maintain the bubble mask 154 in the distal portion 156 of the target tissue focal zone 160. By way of example, in a procedure carried out according to one embodiment, the bubble formation pulse 148 is approximately 0.1 seconds in duration, and is delivered approximately 10 mm distal of the focal center 158 along the transducer propagation axis 152 (see FIG. 12). Because of its relative short duration, it may be desirable in some embodiments to deliver the bubble formation pulse 148 at a higher power than the ablation pulse, although it is not a requirement of the invention.

The bubble formation pulse 148 is immediately followed by an approximately 0.5 second ablation energy pulse delivered to the focal center 158. The transducer is then left off for an approximately 2.0 second delay in order for the bubbles generated in the focal center 158 by the ablation energy pulse to dissipate, and the same cycle is repeated by delivering another 0.1 second bubble formation pulse to the distal region 156, followed by another 0.5 second ablation energy pulse delivered to the focal center 158, and another 2.0 second off period. This series of bubble-masked ablation pulses may be repeated until ablation of the entire the target tissue zone is achieved, which may be verified, e.g., using MRI thermal images.

In accordance with the foregoing embodiment, a procedure for ablating an entire target tissue structure, e.g., a tumor, may comprise performing successive sonications delivered to respective target focal zones that collectively cover the tissue region, each sonication comprising delivering an initial bubble-formation pulse to a relatively distal region of the respective focal zone, immediately followed by a more proximally-focused ablation energy pulse. For each of the respective focal zones, the process of delivering a distal bubble mask pulse, followed by a central ablation pulse, may be repeated until the respective focal zone is completely ablated.

In a variation of the foregoing embodiment, bubbles generated by respective ablation energy pulse may be used as a bubble mask for an ensuing ablation energy pulse delivered to a focal location proximal of the focal location of the present ablation energy pulse. Depending on the size and dimensions of the tissue region to be ablated, as well as on the relative position of the transducer, following an initial bubble-formation pulse in a distal region of a target focal zone tissue region, a two or more sequential ablation energy pulses maybe delivered to locations successively proximal of each immediately preceding pulse, with the tissue bubbles generated from the immediately preceding pulse acting as a respective bubble mask to suppress formation of a far-field energy tail during each present pulse.

For example, with reference to FIG. 10A, a bubble-formation pulse of acoustic wave energy 178 is delivered for approximately 0.1 seconds from a transducer 180 along a transducer propagation axis 182. The bubble formation pulse 178 generates tissue bubbles 187 in a distal region 186 (relative to the transducer 180) of a first target ablation focal zone having a focal center 189. As shown in FIG. 10B, the initial bubble-formation pulse 178 is immediately followed by a delivery of a first (approximately 0.5 second) ablation energy pulse 188 to the focal center 189 of the first target focal zone. As described above, the bubbles generated by pulse 178 suppress formation of a thermal tail by the ablation energy pulse 188. Also, the ablation energy pulse itself generates bubbles 190 in a central focal region 196 of the first target ablation zone, and is immediately followed (as shown in FIG. 10C) by a further ablation energy pulse 198 delivered to a focal center 209 of a second target ablation zone located proximately (relative to the transducer 180) of the first target ablation zone along the propagation axis 182. In this manner, the bubbles 190 in region 196 form a bubble mask to suppress formation of a far-field tail that would otherwise result during ablation pulse 198.

Figure 11:
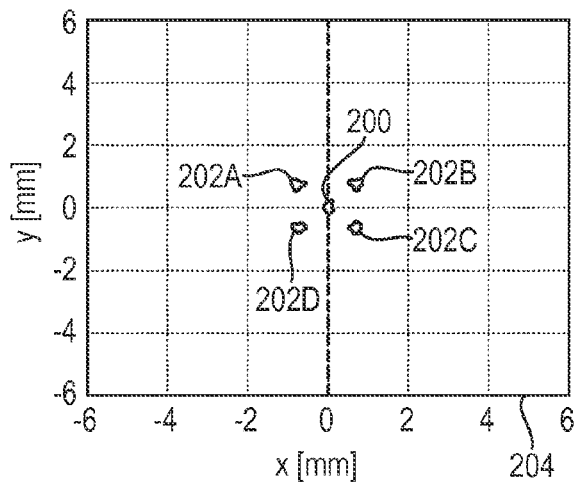
FIG. 11 is a cut-away schematic view of a focal plane of a target tissue ablation zone, illustrating the distribution of a plurality of tissue ablation pulses dithered about the focal center, in accordance with another embodiment of the invention.

In accordance with yet another embodiment, a procedure for treating tissue using acoustic energy includes identifying a three-dimensional target tissue ablation zone, and then delivering respective ablation energy pulses to focal points distributed about a focal center of the target ablation zone. FIG. 11 depicts illustrates one such embodiment, in which a plurality of successive ablation energy pulses 202A-D are delivered to respective focal locations lying in or proximate to a focal plane 204 of a target tissue ablation zone. In particular, the focal plane 204 lies substantially orthogonal to a main focal axis, which passes through (i.e., coming out of or into the figure) a focal center 200 lying in the plane 204. In the illustrated embodiment, the ablation energy pulses 202A-D are distributed in a symmetrical pattern, each located a respective 1 mm in the x direction and 1 mm in the y direction (i.e., for an absolute distance of approximately 1.4 mm) from the focal center 200. The pulses 202A-D are preferably delivered sequentially, for example, each for a duration of between approximately 0.2 second and 1.0 second, with a delay, e.g., of approximately 1.0 to 3.0 seconds interposed between transmission of each successive ablation energy pulse. In one embodiment, the pulses are delivered for approximately 0.5 second each, with an "off-period" delay of approximately 2.0 seconds between successive pulses.

The sequence of ablation energy pulses 202A-D may be repeated, if necessary, until ablation of the entire target tissue focal zone is complete. Alternatively, following delivery of a first sequence of pulses 202A-D, a different sequence may be delivered, e.g., by rotating the focal location of each of the pulses 202A-D by 45°. It has been observed by the present inventors that by dithering the focal locations of the ablation energy pulses about the focal center, formation of a thermal tail along the main focal axis is suppressed. It should be appreciated by those skilled in the art that the particular number, duration, and pattern of the respective ablation pulses in a given sequence may vary, and need not be perfectly symmetrical.

Figure 13:
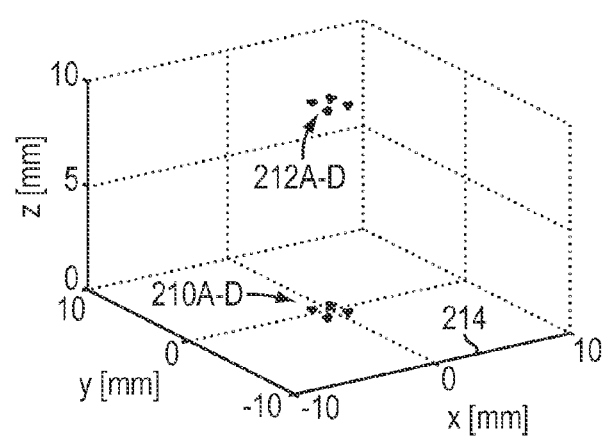
FIG. 13 is a schematic illustration of a three-dimensional coordinate system having an x-y plane at a focal plane of a target tissue ablation zone, with the z-axis extending in a distal direction from the focal plane, illustrating the focal centers of a series of pairs of respective bubble-generating and tissue ablation pulses delivered in accordance with still another embodiment.

In accordance with still another embodiment, in which features of the previously-described embodiments are combined, a procedure for treating tissue using acoustic energy includes identifying a three-dimensional target tissue ablation zone, and then delivering respective bubble-masked ablation energy pulses in a pattern distributed about a focal center of the target ablation zone. By way of example, with reference to FIG. 13, a first (e.g., 0.1 second) bubble formation pulse is delivered along a first axis that is approximately parallel to, but off-center (e.g., 1-2 mm) from, a focal axis of a target ablation zone to a first distal focal location 212A that is (e.g., 10 mm) beyond a focal plane 214 of the target ablation zone. The first bubble pulse is immediately followed by a (e.g., 0.5 second duration) ablation energy pulse delivered along the same first axis to a focal location 210A lying in or proximate the focal plane 214. Following an (e.g., approximately 2.0 second) off-period, the respective bubble formation, ablation pulse and off-period steps are repeated along three further respective axes, each approximately parallel to, but off-center from, the focal axis of the target ablation zone, for a total of four, bubble-masked ablation pulses 210A-D.

In the illustrated embodiment, the respective distal bubble pulses 212A-D and ablation pulses 210A-D are distributed in a similar pattern about the focal center of the target ablation zone (not shown) as pulses 202A-D in FIG. 11. As with that embodiment, the sequence of respective bubble formation and ablation energy pulses 212A-D and 210A-D in the embodiment of FIG. 13 may be repeated, as necessary, until ablation of the entire target tissue focal zone is complete. Alternatively, following delivery of a first sequence of bubble mask-ablation pulses (212A-D and 210A-D), a different sequence of bubble-masked pulses may be delivered, e.g., by rotating the focal locations of the respective pulse pairs 212A-210A, 212B-210B, 212C-210C, and 212D-210D by 45°. It should be appreciated by those skilled in the art that the particular number, duration, and pattern of the respective bubble-masked ablation pulses in a given sequence may vary, and need not be perfectly symmetrical.

The forgoing illustrated and described embodiments of the invention are susceptible to various modifications and alternative forms, and it should be understood ever, that the embodiments described herein are not limited to the particular forms or methods disclosed, but to the contrary, are intended to cover all modifications, equivalents and alternatives falling within the scope of the appended claims.

What is claimed:

1. A method for treating body tissue using acoustic energy, comprising:
   identifying a target focal zone to be treated;
   delivering a first pulse of acoustic energy from a transducer to generate bubbles in bodily liquid contained in the tissue in a tissue region located distally, relative to the transducer, of a focal center of the target focal zone; and
   before the distally located bubbles dissipate, delivering a second pulse of acoustic energy from the transducer to generate thermal ablation energy in tissue at or proximate the focal center of the target focal zone,
   wherein the first pulse is focused at a selected distance from the focal center of the target focal zone to cause the distally located bubbles to suppress formation of a far-field thermal-ablation tail; and further wherein the bubbles are generated in the body liquid without using an injected fluid.

2. The method of claim 1, wherein the first energy pulse is delivered along a transducer propagation axis passing through a focal plane containing the focal center, and wherein the first pulse is focused along the propagation path between approximately 5 mm and approximately 15 mm distal of the focal plane.

3. The method of claim 2, wherein the first pulse is focused along the propagation axis approximately 10 mm distal of the focal plane.

4. The method of claim 1, wherein the first pulse is delivered at a higher power than the second pulse.

5. The method of claim 1, wherein the first pulse has a duration between approximately 0.05 second and approximately 0.15 second, and the second pulse has a duration between approximately 0.20 second and approximately 1.0 second.

6. The method of claim 5, wherein the first pulse has a duration of approximately 0.10 second, and the second pulse has a duration of approximately 0.5 second.

7. The method of claim 1, wherein the second pulse generates bubbles in tissue in the target focal zone, the method further comprising delivering a third pulse of acoustic energy from the transducer before the bubbles generated by the second pulse have dissipated, the third pulse being focused proximally of the focal center to generate thermal ablation energy in tissue proximal of the target focal zone.

8. The method of claim 1, further comprising:
following delivery of the second pulse of acoustic energy, delivering a third pulse of acoustic energy from the transducer to generate bubbles in the distal tissue region, and
delivering a fourth pulse of acoustic energy from the transducer before the bubbles generated by the third pulse have dissipated, the fourth pulse being focused at or proximate the focal center to generate thermal ablation energy in tissue.

9. A focused ultrasound system for treating tissue using acoustic energy, comprising:
a transducer configured for delivering acoustic energy to internal body tissue; and
a controller for controlling delivery of acoustic energy by the transducer, the controller configured to
identify a target focal zone having a focal center;
cause delivery of a first pulse of acoustic energy from the transducer to generate bubbles in bodily liquid contained in tissue located in a tissue region located distally of the focal center relative to the transducer; and
before the distally located bubbles dissipate, cause delivery of a second pulse of acoustic energy from the transducer to generate thermal ablation energy in tissue at or proximate the focal center of the target focal zone, wherein the first pulse is focused at a selected distance from the focal center of the target focal zone to cause the distally located bubbles to suppress formation of a far-field thermal-ablation tail; and further wherein the controller is configured to generate bubbles in the body liquid without using an injected fluid.

10. The system of claim 9, wherein the controller is configured to deliver the first energy pulse along a transducer propagation axis passing through a focal plane containing the focal center, with the first pulse being focused between approximately 5 mm and approximately 15 mm distal of the focal plane.

11. The system of claim 9, wherein the first pulse has having a duration between approximately 0.05 second and approximately 0.15 second, and the second pulse has a duration between approximately 0.20 second and approximately 1.0 second.

12. The system of claim 9, wherein the controller causes delivery of the respective first and second pulses, at least in part, based on input received through a user-interface.

13. The system of claim 9, wherein the controller is configured to automatically cause delivery of the respective first and second pulses.

14. A method of treating body tissue using acoustic energy, comprising:
identifying a plurality of focal zones to be treated with acoustic energy delivered by a transducer; and
for each focal zone, delivering a bubble-formation pulse of acoustic energy from the transducer to generate bubbles in bodily liquid contained in the tissue in a tissue region located distally of a focal center of the respective focal zone and, before the bubbles have dissipated, delivering an ablation pulse of acoustic energy focused at the focal center of the respective focal zone and not in the distally located tissue region to generate thermal ablation energy therein, wherein the bubble formation pulse is focused at a selected distance from the focal center of the respective focal zone to cause the distally located bubbles to suppress formation of a far-field thermal-ablation tail; and further wherein the bubbles are generated in the body liquid without using an injected fluid.

15. The method of claim 14, wherein the respective ablation pulses are delivered for a substantially greater duration than the respective bubble-formation pulses.

16. A method of treating tissue using acoustic energy, comprising:
identifying a target focal zone in a tissue region to be treated, the target focal zone having a focal plane and a focal center lying in the focal plane;
delivering a first pulse of acoustic energy from a transducer to generate bubbles in body liquid contained in a region located distally, relative to the transducer, of the focal center of the target focal zone;
before the distally located bubbles dissipate, delivering a plurality of ablation pulses of acoustic energy to locations lying in or proximate the focal plane and distributed in a substantially symmetrical pattern about the focal center; wherein the first pulse is delivered prior to each ablation pulse and is focused at a selected distance from the focal center of the target focal zone to cause the distally located bubbles to suppress the formation of a far-field thermal ablation tail; and further wherein the bubbles are generated in the body liquid without using an injected fluid.

17. The method of claim 16, wherein the ablation pulses are delivered sequentially.

18. The method of claim 17, wherein a delay period is interposed between delivery of successive ablation pulses.

19. The method of claim 18, wherein each of the ablation pulses is delivered for a duration between approximately 0.2 second and 1.0 second, and wherein the delay between successive ablation pulses is between approximately 1.0 second and approximately 3.0 seconds.

20. The method of claim 16, wherein the respective ablation energy pulses are delivered for a greater duration than the respective bubble-formation pulses.

21. The method of claim 20, wherein the respective bubble formation pulses each a duration between approximately 0.05 second and approximately 0.15 second, and the respective ablation pulses each a duration between approximately 0.20 second and approximately 1.0 second.

22. The method of claim 16, wherein the respective bubble-formation pulses are focused between approximately 5 mm and approximately 15 mm distal of the focal plane.

* * * * *

UNITED STATES PATENT AND TRADEMARK OFFICE
CERTIFICATE OF CORRECTION

PATENT NO. : 8,235,901 B2
APPLICATION NO. : 11/536619
DATED : August 7, 2012
INVENTOR(S) : Rita Schmidt et al.

Page 1 of 1

It is certified that error appears in the above-identified patent and that said Letters Patent is hereby corrected as shown below:

In the Claims:

Column 10 Claim 20, line 49-50, should read:
--ablation pulses are delivered--

Signed and Sealed this
Thirtieth Day of April, 2013

Teresa Stanek Rea
*Acting Director of the United States Patent and Trademark Office*